United States Patent
Krutchinsky et al.

(10) Patent No.: US 7,012,249 B2
(45) Date of Patent: Mar. 14, 2006

(54) HIGH CAPACITY AND SCANNING SPEED SYSTEM FOR SAMPLE HANDLING AND ANALYSIS

(75) Inventors: Andrew Krutchinsky, New York, NY (US); Brian Chait, New York, NY (US)

(73) Assignee: The Rockefeller University, New York, NY (US)

( * ) Notice: Subject to any disclaimer, the term of this patent is extended or adjusted under 35 U.S.C. 154(b) by 0 days.

(21) Appl. No.: 10/924,269

(22) Filed: Aug. 23, 2004

(65) Prior Publication Data

US 2005/0077460 A1    Apr. 14, 2005

Related U.S. Application Data

(63) Continuation of application No. 09/737,660, filed on Dec. 15, 2000, now abandoned.

(51) Int. Cl.
*B01D 59/44*    (2006.01)

(52) U.S. Cl. ............... 250/288; 250/310; 250/311; 250/281

(58) Field of Classification Search ........... 250/288
See application file for complete search history.

(56) References Cited

U.S. PATENT DOCUMENTS

| | | | | | |
|---|---|---|---|---|---|
| 4,843,243 | A | * | 6/1989 | Biemann et al. | 250/341.8 |
| 5,413,939 | A | * | 5/1995 | Gustafson et al. | 436/518 |
| 5,715,051 | A | * | 2/1998 | Luster | 356/239.1 |
| 5,898,181 | A | * | 4/1999 | Vurens | 250/559.28 |
| 6,327,031 | B1 | * | 12/2001 | Gordon | 356/72 |
| 6,356,346 | B1 | * | 3/2002 | Hagen et al. | 356/237.1 |

* cited by examiner

*Primary Examiner*—Nikita Wells
*Assistant Examiner*—Anthony Quash
(74) *Attorney, Agent, or Firm*—Klauber & Jackson (57) ABSTRACT

Disclosed is an apparatus for examining and inspecting at least one sample in order to determine characteristics of the sample having the a support for receiving a compact disc, the compact disc having deposited on a surface thereof at least one sample, inspection means for effecting a physical change in at least one sample, the inspection means positioned for registration with the surface of the compact disc bearing at least one sample; and a traversal mechanism adapted for reciprocating movement, to move the sample in and out of the path of the inspection means.

20 Claims, 6 Drawing Sheets

HIGH CAPACITY AND SCANNING SPEED SYSTEM FOR SAMPLE HANDLING AND ANALYSIS

The research leading to the present invention was supported, at least in part, by NIH Grant No. RR 00862. Accordingly, the Government may have certain rights in the invention. This application is a continuation of U.S. application Ser. No. 09/737,660, filed Dec. 15, 2000, now abandoned.

GOVERNMENTAL SUPPORT

FIELD OF THE INVENTION

The present invention is directed to the field of analytical devices typically found in a laboratory, and in particular, a research laboratory directed to, among others, the chemical, biological, biochemical, and medical arts. More particularly, the device is an apparatus which includes a sample located upon the surface of a compact disc, and a mechanism which drives the sample on the disc surface in and out of the path of an inspection means that derives information about the properties and characteristics of the sample. To provide but one of many possible embodiments as an example, the analytical device could be a mass spectrometer, and the inspection means could be an ion source that interacts with the sample to create a charged particle or particles analyzed by any of the known mass spectrometer analyzers.

BACKGROUND OF THE INVENTION

The modern scientist has many analytical tools available at his or her disposal, each of which can provide useful information about a sample, whose identities may or may not be known. Aside from using these tools to learn the identity of a sample the tools may provide information such as molecular weight of the sample, functional groups possessed by the sample, and position of the groups, all of which are valuable in determining molecular structure. To give but one of the example of how these tools can be used, they can also be used to determine sample purity, where the identity of the sample is known.

The analytical devices include mass spectrometers, UV spectrometers, fluorescence detectors, infrared spectrometers, visible light spectrometers, RAMAN spectrometers, and atomic force microscopes. Certain of these devices, such as the mass spectrometer and the RAMAN spectrometer, employ, or can employ a laser to interact with the sample under analysis.

At it simplest, mass spectroscopy is a technique that provides the measure of a mass of a molecular sample. Additionally, important structural information can be obtained about samples whose identities are unknown by measuring the masses of fragment ions produced from the sample.

In a mass spectrometer, magnetic and electric fields are used to apply force to charged particles, that is, ions, which are in a vacuum. The target sample is ionized, and the ions, which are in the gas phase, are introduced into the vacuum system of the mass spectrometer. This is easily done for gaseous or heat-volatile samples. However, many analytes decompose upon heating. These kinds of samples require either desorption or desolvation methods if they are to be analyzed by mass spectrometry. Although ionization and desorption/desolvation are usually separate processes, the term "ionization method" is commonly used to refer to both ionization and desorption (or desolvation) methods.

The choice of ionization method depends on the nature of the sample and the type of information required from the analysis. In one known technique, the molecules of interest are ionized by energetic electron collision so that the ions produced from the sample may be steered through the mass spectrometer apparatus and then detected by a detector. However, the energetic electron collision is disadvantageous in that molecules are broken apart, or "fragmented" as a result of the collision, and the resulting mass spectrum must be interpreted in the light of the resulting "fragmentation pattern" which results for the electrons. On the other hand, ionization methods such as matrix-assisted laser desorption ionization (MALDI) and electrospray ionization (ESI) tend to produce mass spectra from involatile compounds like peptides, proteins, and DNA, with little or no fragment ion content.

When employing ESI, a sample solution is typically sprayed from a hollow needle into an orifice across a high potential difference (i.e, on the order of several kilovolts). Heat and gas flows are used to desolvate the ions existing in the sample solution droplets. Electrospray ionization can produce multiply charged ions with the number of charges tending to increase as the molecular weight increases. Electrospray ionization is effective for charged, polar and basic compounds, and permits the detection of high-mass compounds at mass-to-charge ratios (m/z) that are easily determined by most mass spectrometers (m/z typically less than 4000). It is an effective method for analyzing both singly and multiply charged compounds. The low chemical background leads to excellent detection limits, and the presence or absence of fragmentation can be controlled by adjusting the energy input into the ions.

Direct laser desorption relies on the very rapid heating of the sample or sample substrate to vaporize molecules so quickly that they do not have time to decompose. This is effective for low to medium-molecular weight compounds. Another laser desorption technique, known as matrix-assisted laser desorption ionization (MALDI), relies on the absorption of laser energy by a matrix compound. That is, the sample is dissolved in a solution containing a large molar excess of a matrix-forming material that strongly absorbs light at the laser wavelength. A small amount of this solution is placed on the laser target and dried. The matrix absorbs the energy from the laser pulse which results in the vaporization and ionization of the analyte. Again, with MALDI and ESI, little or no fragmentation occurs when the sample is ionized. This is a desirable attribute as these techniques are well suited for the analysis of relatively high molecular weight compounds, such as in the analysis of proteins.

One of the difficulties of current mass spectrometer instruments is in the translation or movement of samples in and out of the energy source that effects ionization. For example, in a laser desorption method, the laser and/or sample must move in order to scan the particular material. Such movement should be rapid while, at the same time being accurate, repeatable, and reliable. This is particularly true in the instances where a large number of samples are to be targeted, requiring considerable movement of the laser in order to transfer energy to all available samples. It is often necessary to hit each given sample about 100 times to yield good results. When, in a given session, a significant number of samples are the subject of analysis, this could mean that hundreds or thousands of hits must be achieved. It is therefore evident that a mechanism must be supplied to carry out a rapid, accurate translation of the samples across the laser beam.

Compact discs are currently used in various ways, typically as a data storage medium. There are various translation system or disc drives that have been developed at great cost for the music and computer industry to read the information from such compact discs. In general, such compact discs are a standardized size, having a diameter of about 12 cm. Add a thickness of about 1.2 mm. The compact disc is provided with a storage medium into which pits or depressions are made to produce light reflectivities that vary and correspond to digitized data. Thus, there are a number of fairly standard drives commercially available to read the discs. The drives are provided with means that move the disc through the path of a scanning laser. Typically, the disc rotates through the path at 200 to 500 rpm. Also, the drive is typically provided with means to move the laser radially with respect to the disk, across the surface of the disc, typically from the inside of the disc to the outside of the disc. The laser reads the differences in reflectivity from the pits or depressions that have been created within the recording medium that is embedded within the disc. The differences are converted into usable information, whether it be sound, text, or graphics, to name just a few of many possibilities. Present commercial disc drive systems can be used to translate the current laser diode to any position on the compact disc by automatic moving systems at the behest of an electronic input.

With present translation systems, such as those used in the MALDI mass spectrometer system, movement or translation is effected in a device capable of x-y translation wherein the device is typically moved by means of stepper motors that can move the sample or samples, or energy source, along the x and the y axes. The motion of such translation devices is indexed, that is, one step at a time and requires considerable speed to be able to move the samples quickly through the analysis process. Such translation devices and the analysis equipment using stepper motors are generally quite heavy, cumbersome and contain a considerable number of moving parts and components, any one of which can become potential source of failure.

It would be advantageous to be able to carry out a rapid scanning of a large number of samples rapidly, accurately and with great reproducibility.

SUMMARY OF THE INVENTION

In one embodiment, the present invention is an apparatus which includes a sample located upon the surface of a compact disc, and a mechanism which drives the disc, and thereby the sample, in and out of the path of an inspection means. The inspection means derives information about the properties and characteristics of the sample. To provide but one of many possible embodiments as an example, the analytical device could be a mass spectrometer, and the inspection means could be an ion source that causes the sample to be volatilized and ionized so that the resulting ions can be analyzed by any of the known mass spectrometer analyzers.

The analytical devices include mass spectrometers, UV spectrometers, fluorescence detectors, infrared spectrometers, visible light spectrometers, RAMAN spectrometers, and atomic force microscopes. Certain of these devices, such as the mass spectrometer and the RAMAN spectrometer employ, or can employ, a laser as the inspection means. Generally speaking "inspection means" can be defined as a probe which interacts with the sample under analysis to yield desirable information about the sample. In some instances, the sample may undergo a transformation due to the interaction with the inspection means, such as when a sample is ionized or otherwise converted into charged particles, which can occur in a mass spectrometer analysis. It is also possible that the inspection means may undergo a transformation, such as when a portion of the infrared spectrum is absorbed by the sample when conducting IR spectrometric analysis. To give some examples without necessarily accounting for all possibilities, the inspection means may be electrons, or other charged particles, which may be used in, among other devices, mass spectrometers. The inspection means my be some kind of electromagnetic radiation, such as the infrared, ultraviolet, visible light, or the aforementioned laser light sources.

In another embodiment, the present invention relates to a system for the analysis of samples to determine their mass using a mass spectrometer, and/or to learn other useful information about the samples, including but not limited to information concerning their chemical compositions and molecular structure. Particularly, the invention relates a system that utilizes mass spectrometry techniques in conjunction with a high speed translation system, that is, system of movement, to facilitate rapid and accurate positioning of a sample deposited on a compact disc.

In another embodiment, the present invention is an apparatus used in delivering samples to the inspection means in a mass spectrometer. In one embodiment, the device is a compact disc having samples positioned on the inspection means-facing side of the disc and a disc driver which moves the disc, and therefore the samples positioned on the disk, in and out of the path of the inspection means. In another embodiment, movement of the disc, and hence the samples, is effected by rotating the disc, or moving the disc in a direction corresponding to the radius of the disc. In yet another embodiment, the inspection means is movable, such as in a path that traverses the radius of the disc, or movable by a system of x-y translation. In a still further embodiment, the laser diode can be replaced by a Fisher Optic UV laser coupled through a fiber optic link to the movable head. In yet another embodiment, the samples are ionized by laser desorption, in which a laser is used as the inspection means. In another embodiment employing laser desorption, the technique used is matrix-assisted laser desorption ionization (MALDI). In yet a further embodiment, the apparatus is provided with a mechanism that allows movement of the disc, and hence movement of the samples in and out of the ionization effector. In yet a further embodiment, the apparatus is provided with a manual mechanism which permits the operator of the device to manually move the disc, and hence move the samples in and out of the ionization source. Yet a further embodiment is a mass spectrometer containing any of the aforedescribed features.

The present commercially available disc drives that move the compact disc and read information from the disc provide an efficient, accurate system for carrying out the movement associated with the inspection of the disc by the inspection means. Further, where the inspection means is a laser source, such drives already include an inspection means.

The delivery device is a translation system that can be used with virtually any type of analytical device, such as those previously enumerated. With respect to a mass spectrometer, any technique of directing the charged particles to the detector can be used, and any possible inspection means can be used in ionizing to the sample target. Particularly, the present invention can be used with time of flight (TOF), quadrupole, quadrupole TOF, quadrupole-quadrupole TOF (qqTOF), magnetic sector, and ion trap mass analyzers.

Thus, by the use of a compact disc to hold the sample for analysis, the translation device employed in the present invention can be used with the commercial disc drivers that are currently available at a relatively low cost and yet are extremely versatile in their ability to locate any desired location on the surface of the disc to direct the beam of a laser. Typically the laser used with current disc reading systems can be positioned to direct that laser beam onto a rotating disc and directed to any location on the compact disc surface. Accordingly, with the present system, the technique of translation of a compact disc is utilized by placing a sample to be analyzed on the surface of the compact disc and an intermittent laser beam is directed to impinge upon that sample to carry out the analysis by means of mass spectrometry.

Any known means can be employed in depositing samples sprayed on the disc. For example, the samples can be spray deposited as an aerosol, ultrasonically deposited, or deposited with a micropipette or fine needle, or any other known means. Further, it is possible to deposit the sample by use of an ink jet or piezoelectric device, these devices can be used to coat discs with fine droplets of sample.

In a further embodiment, the samples are discreetly arrayed over the surface of the disk. That is, spaces are present between individual sample deposits. Also, continuous deposition, e.g. from the eluent of a chromatographic (e.g. HPLC) or electrophoretic (e.g. capillary electrophoresis) apparatus, can be employed. In yet a further embodiment the samples are associated with digital information stored on the disk in a machine readable format. The information may come in a variety of forms. For instance, the information may be used to identify the exact or approximate locations of samples(s) on the disk. It may identify a serial number or the like that has been assigned to a particular sample. It may provide instructions to the laser about when to fire at the sample, and for how long. Also, such information may instruct the disc drive. For example, such information may provide the commands to the disc drive regarding (1) the drive's movement, and at what time movement should occur, (2) when the drive should to stop moving, and (3) the speed at which the drive should move. Such information may be deposited on the same disc side as the samples, or on opposite sides of the disc, in which case an additional laser would be present to read the other side of the disc where information is stored. In this case the reading of the information stored on one side of the disc by a first laser could be used to activate a second laser on the other side in order to investigate and analyze a given sample deposited on the sample side of the disc.

As such the highly commercial disc drivers used with CD players and procurable at a relatively low cost can be used to drive the disc on which the sample is located and well known analytical techniques can be employed to determine characteristics, properties, and identity of the samples.

By the present use of a high speed disc driver, the overall apparatus can direct the laser onto the large number of samples accurately and quickly so as to enable the analysis of an extremely large number of samples within a short period of time.

DETAILED DESCRIPTION OF THE PREFERRED EMBODIMENT

Figure 1:
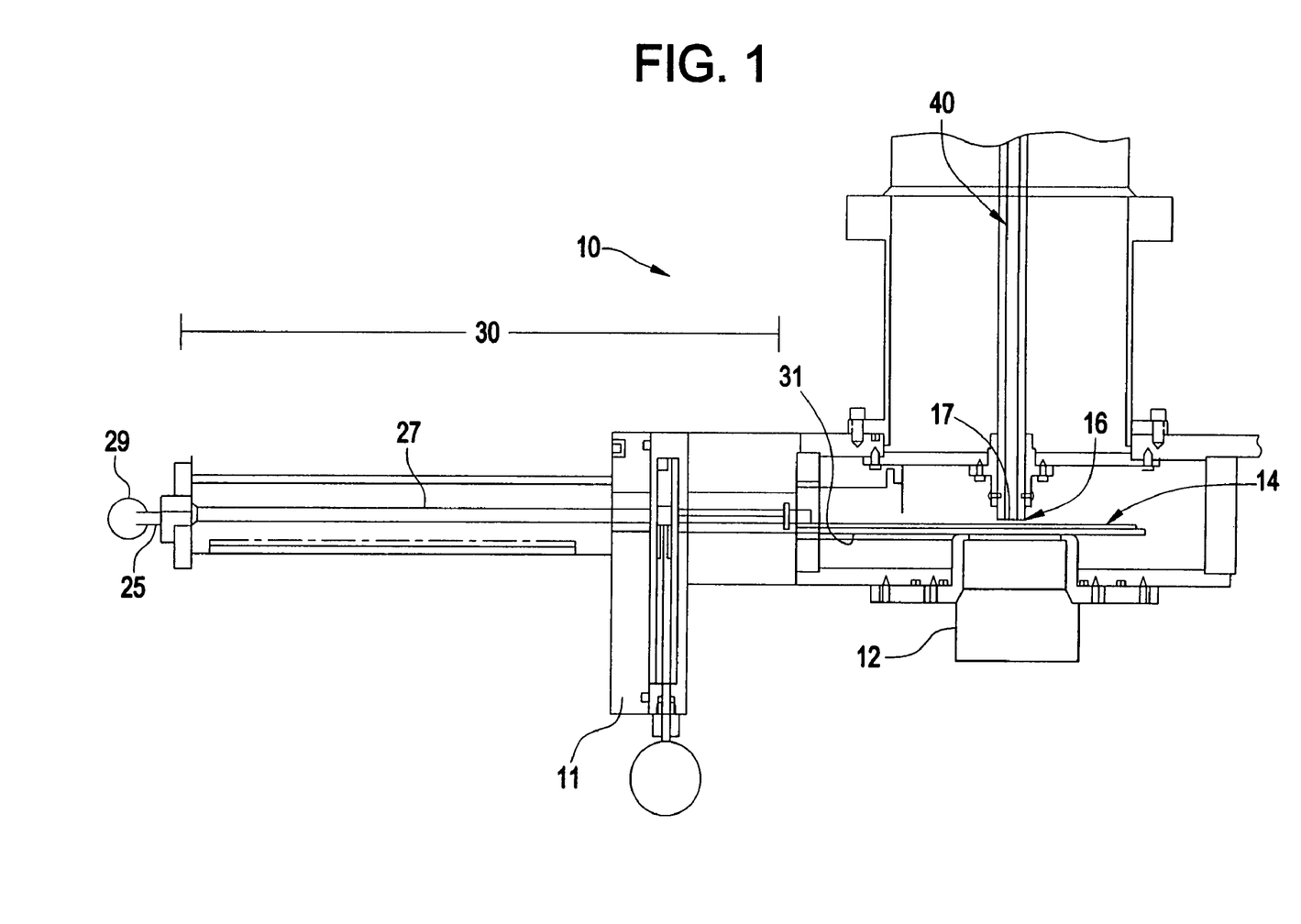
FIG. 1 is a schematic of a mass spectrometer which includes embodiments of the present invention.

The present invention will be described in relation to a mass spectrometer, but the analytical device could be a UV spectrometer, a fluorescence detector, a mass spectrometer, an infrared spectrometer, a visible spectrometer, a RAMAN spectrometer, a surface plasmon resonance apparatus, and an atomic force microscope. FIG. 1 depicts a mass spectrometer 10 containing features of the present invention. This particular analyzer has a quadrupole ion guide in its first stage, but as previously noted, this is not an essential feature since any kind of analyzer can be used with the present invention. The spectrometer is provided with a disc drive 12 into which a compact disc 14 is placed. The drive may be a conventional disc drive provided with a sliding tray that moves the disc from a first position where it is outside the drive (the load/unload position) and a second position where it is in position to register with the inspection means, which in this case is a laser 22. As noted, the inspection means can be any of those appreciated by the skilled artisan. The disc drive provides means for rotating the disc and moving the laser or a fiber optic energy source attached to the laser in a path that traverses the radius of the disc. In another embodiment the laser or a fiber optic energy source attached to the laser can be attached to a guide track or the like and can be moved according along x-y coordinates. In another embodiment the laser beam can be kept in a fixed position and the whole CD drive mechanism translated so as to access all positions from the center of the CD to its outer edge.

In the case of a mass spectrometer, a vacuum must be provide to reduce pressure in the spectrometer to the customary operating values. Therefore, it is advantageous to seat the disc drive within the vacuum chamber 30. Once the disc is loaded into the drive, the chamber 30 is sealed, and the spectrometer is evacuated by valve 11 at a time prior to commencing the inspection of the samples.

The compact disc 14 upon which samples 17 have been deposited is moved by the driver 12 to a position within the path of the inspection means 16, which again, is shown here as a laser source. The laser energy source, is focused to a relatively small diameter, for example, in the range of $1\mu$ to $1000\mu$. The samples are moved in and out of the path of the inspection means by rotation of the driver 12 which rotates the disc at speeds typically attained by CD drives, i.e.-200 r.p.m. to 500 r.p.m.

The skilled artisan would readily appreciate that a source 14 other than a laser, or in addition to a laser, could be employed, such as a source which generates energetic collisions or which employs ESI sources. In the case of a mass spectrometer, the laser can be a pulsed laser with short duration pulses (psec to $\mu$sec in duration) and the timing of the laser pulses correlated with the motions of the CD so as to hit any desired spot on the CD surface.

In a further embodiment, the disc can be moved from side to side by manual manipulation of a joy stick 25. The joy stick is a rod 27 pivotable about an axis having a knob 29 at one end to facilitate gripping and rotation, and a disk 31 at the opposite end which contacts the outer edge of the disc. Rotating the knob 29 rotates the rod 27 and disc 31, and this rotational movement is translated to the disc, as it rotates by virtue of contact with the disc.

The laser beam is positioned to hit a target on the disc located at the entrance to the analyzer, shown in FIG. 1 as a quadrupole 40. Again, where the analytical device is a mass spectrometer, the analyzer does not have to be a quadrupole analyzer, since any kind of analyzer can be used with the present invention, such as a time of flight (TOF), quadrupole TOF quadrupole-quadrupole TOF (Qq TOF), magnetic sector, and ion trap mass analyzers. The samples are desorbed from the disc as energy is transferred to the samples, and enter the analyzer. A video camera can be used to monitor the sample and the laser hitting the sample.

Figure 2:
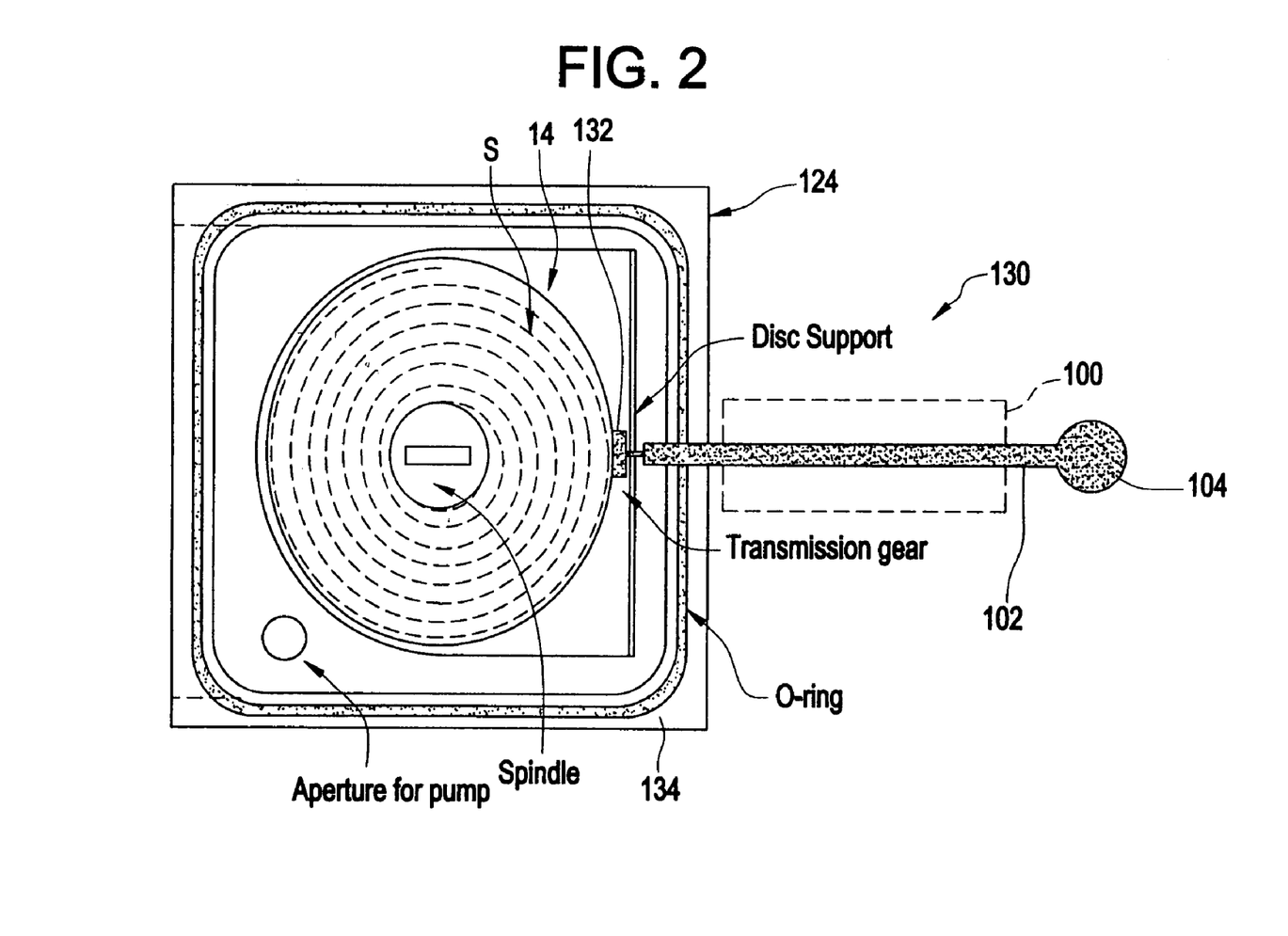
FIG. 2 is a top plan view of an embodiment of the present invention.
Figure 3A:
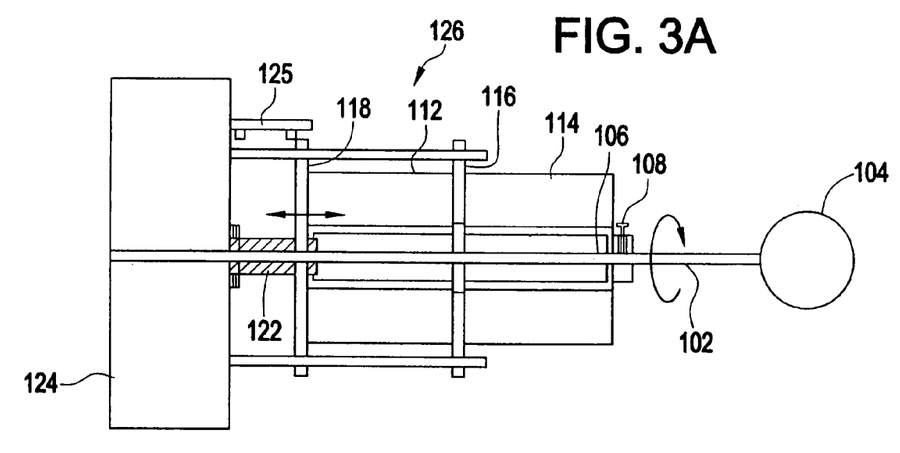
FIGS. 3A and 3B are side elevational views of a motorized manipulator used in certain embodiments of the present invention.
Figure 3B:
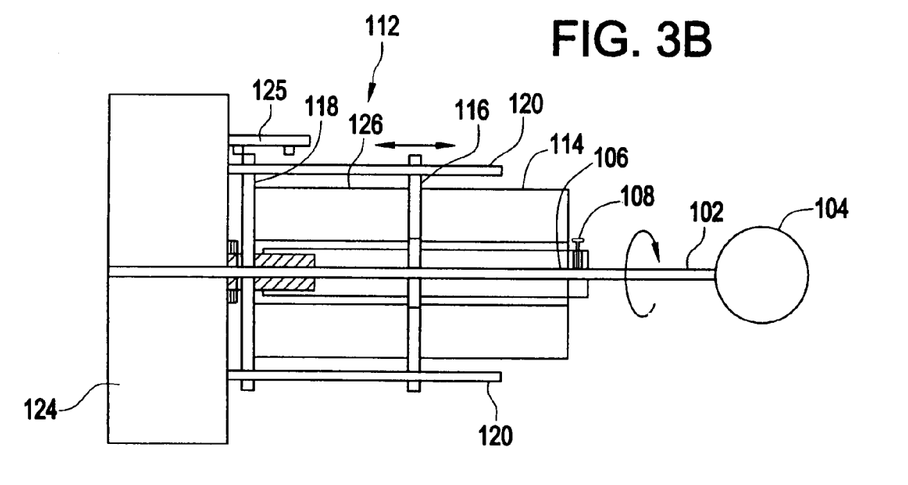

FIGS. 2 and 3 depict an embodiment of the present invention in which the joystick, a/k/a the target shaft 102, can be operated manually, or can be operated by a motorized manipulator assembly 100. One end of the target shaft is situated within the cassette 130 in which the CD is housed. A rotating wheel 132 resting upon the CD extends from this end of the target shaft, so that rotation of the shaft rotates the wheel, thereby rotating the disc and turntable underneath the disc. The shaft passes through an O-ring 134 or other sealing element that seals interior of the cassette from the outside environment.

A slit 136 is provided on a side of the cassette 130 across from the side where the target shaft 102 is located. The CD can be loaded into the cassette through the slit. The cassette is provided with a turntable (not shown, as the Figure shows a CD resting upon the turntable). At the center of the profile a circular pedestal is provided over which the opening in the compact disc is situated.

The cassette is further provided with an aperture into which a pump can be inserted in order evacuate the cassette.

The sample containing CD can either be moved by hand or by a motorized manipulator. In the case of the latter, the motorized manipulator is constructed of two hollow-shaft "inside/out" stepper ("IOS") motors, which are available from Intelligent Motion Systems. The location of a suitable motorized manipulator assembly 100 is shown in FIG. 2 and its construction is depicted in FIGS. 3A and 3B, with the manipulator in an in position (3A) and in an out position (3B). A target shaft 102 extends through both motors. A knob 104 is provided on the shaft end that extends out of the manipulator assembly. The knob 104 provides a way to rotate the target shaft in the manual mode of operation. The target shaft passes into the manipulator assembly 100 through inlet 106. A shaft lock/release screw 108 extending perpendicular to the target shaft 102, or substantially perpendicular thereto, is positioned in a bore 110 in the inlet 106. When the shaft lock/release screw 106 is tightened against the target shaft, the second IOS motor 114 can rotate the target shaft because the shaft lock/release screw 106 fixes the shaft to the rotating interior of the motor. When the target CD is removed or installed, the shaft lock/release screw 106 is loosened such that the target can manually be moved to its outmost position, allowing the vacuum lock to be operated.

Translation of the target shaft is controlled by first IOS motor 112 and rotation is controlled by second IOS motor 114. Bearing plate 116 joins motors 112 and 114, which together with a second bearing plate 118 on first IOS motor 112, allows the motor construction to slide on glider rods 120. Hollow ball screw 122, fixed to the CD-cassette 124, is screwed into or out of IOS 1 when the CD target is translated. The target shaft 102 is moved through the ball screw 122 and through the vacuum sealing of the cassette 124. The two micro switches 125 mounted onto a board 126 extending from the target cassette define the home positions of the manipulator. A computer supervised driver circuit (not shown) controls all action of the motorized manipulator.

The applicants have found that a Finnegan Mat LCQ ion trap mass spectrometer and a Sciex QqTOF mass spectrometer are well suited to be adapted to receive the compact disc systems described herein. In the case of the mass spectrometer, the laser can be a pulsed laser with short duration pulses (psec to psec duration) and the timing of the laser pulses correlated with the motions of the CD so as to hit any desired spot on the CD surface.

The CD's used in the present invention can be provided with a clear polycarbonate surface, such as a surface of LEXAN® clear plastic sheeting. The CD's may also be provided with a coating of a metallization layer over the data layer to enhance reflectivity.

Figure 4:
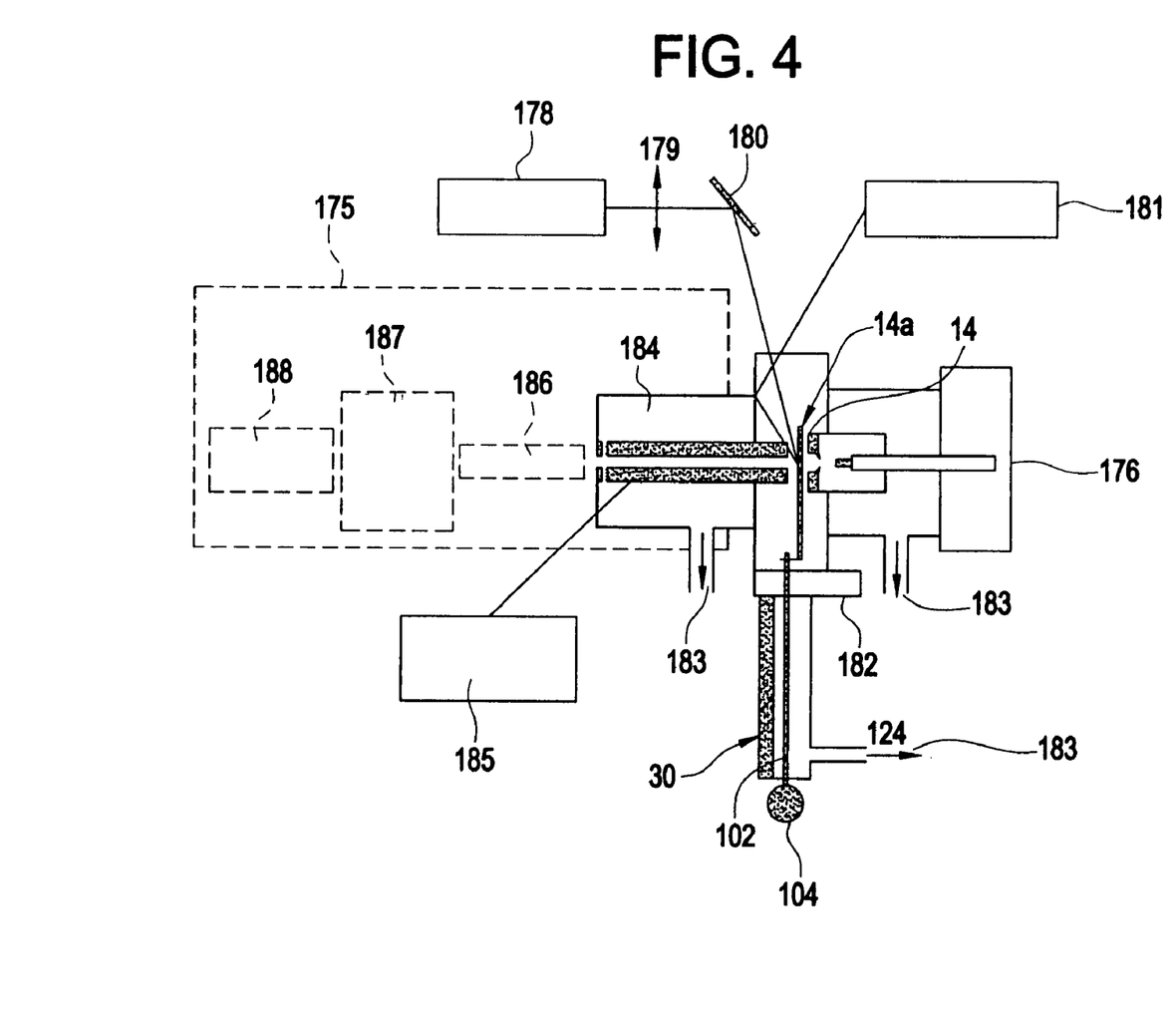
FIG. 4 is a perspective view of a further embodiment of the present invention.
Figure 5:
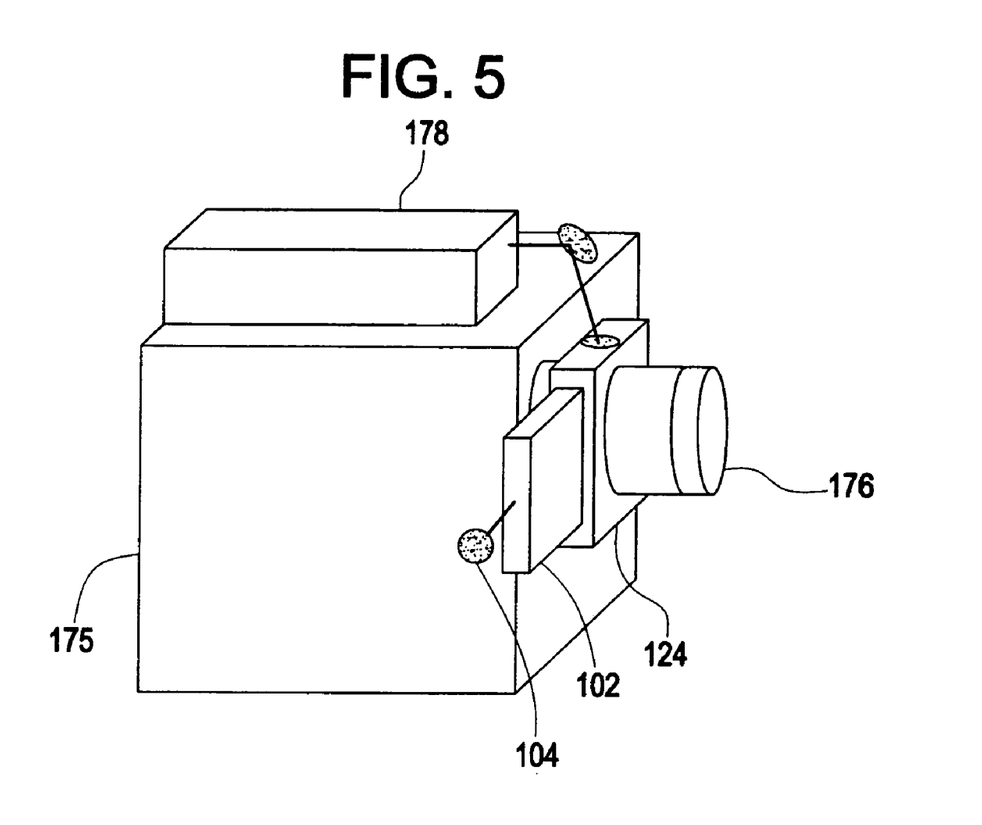
FIG. 5 is a perspective view of a further embodiment of the present invention.

In a further embodiment shown in FIGS. 4 and 5, the invention is a mass spectrometer 175, such an LCQ system which incorporates an electrospray ion source (ESI) 176, in addition to the MALDI target cassette 124 previously shown and described. Such a system, which incorporates the components of an LCQ system. Other system components include: $N_2$ laser 178, lens 179, mirror 180, video camera 181, compact disc 14, MALDI target on compact disc 14a, valve 182, X/L min pumps 183, MALDI target cassette 124, target shaft 102, knob 104, quadrupoles 184, quadrupole power supply 185, octopoles 186, ion trap 187, and detector 188.

Figure 6:
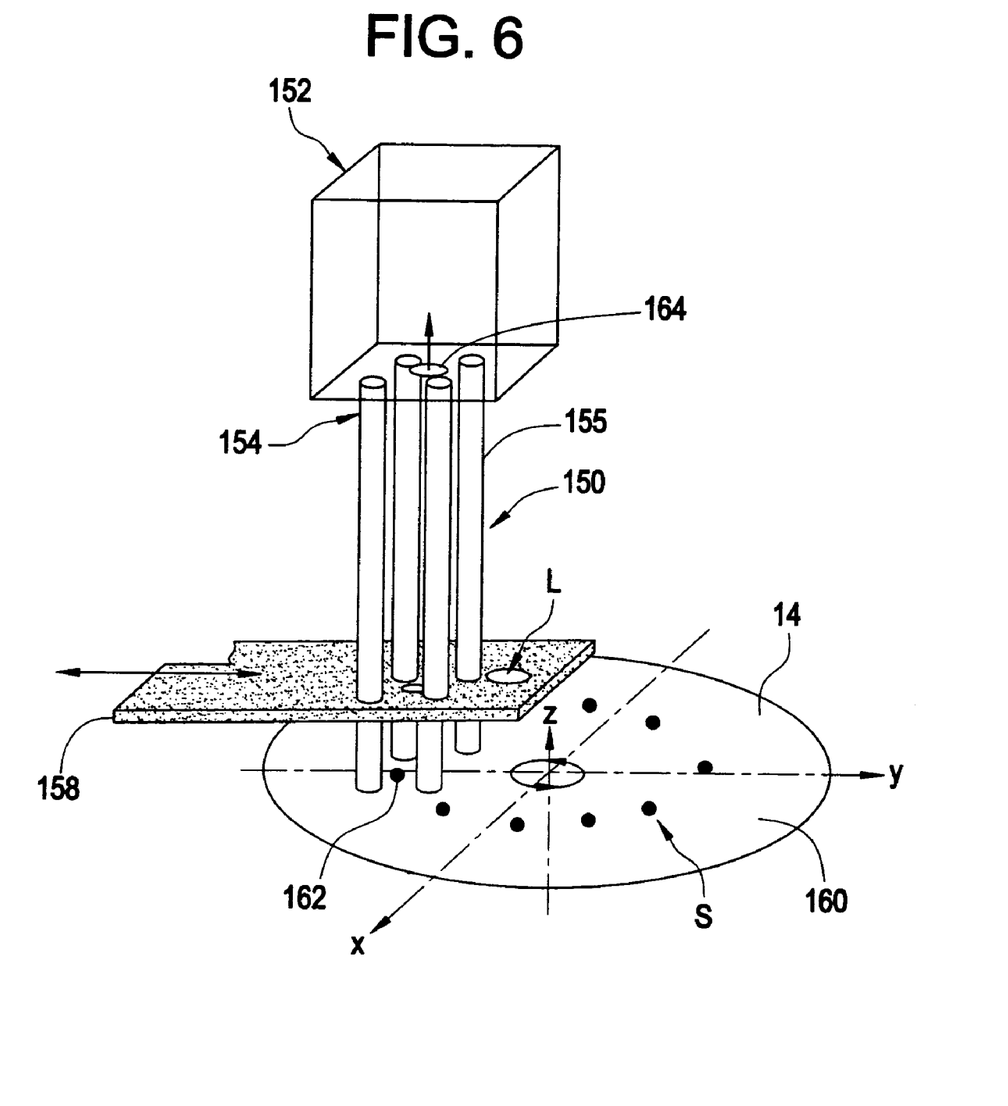
FIG. 6 is a perspective view of a yet a further embodiment of the present invention.

FIG. 6 shows a scanning assembly 150. The assembly which scans the samples can be configured in several ways. For instance, the mass spectrometer 152 and the multiple ion guide 154 constructed of a plurality of rods 155. Here, a quadrupole arrangement is shown, but other arrangements, such as an octopole arrangement, is possible. A focusing lens 156 that directs laser light can be fixed in a positioning guide 158. When the samples S on the disc 160 are scanned, the disc 160 is rotated about the Z axis and moved in the direction of the X axis, the Y axis, or both. Movement of the disc in this manner positions the samples at the entrance of the multipole ion guide.

In another arrangement, the disc 160 cannot move in the X and Y directions, but is able to rotate around the Z axis. Samples located on the disc surface are scanned by moving the positioning guide 158 along the X axis, Y axis, or both, so as to position each new sample at the entrance 162 of the multipole ion guide 154.

In yet another arrangement, the disc 160 cannot move in the X and Y directions, but is able to rotate around the Z axis. To scan the samples S arrayed on the surface of the disc 160, the positioning guide is moved. Here, however, the output 164 of the ion guide is fixed at the entrance to the mass spectrometer 152. The positioning guide 158 is moved, in turn moving the input 162 of the ion guide and the lens 156. These components can be moved in the X direction, the Y direction, or both, so that each sample on the disc can be positioned at the entrance of the multipole ion guide. It should be evident that in this arrangement, with the ion guide fixed at one end and movable at the other end, that the multipole ion guide rods are flexible. To facilitate this the multiple ion guide can be constructed of flexible cylindrical springs or flexible metallized tubes, instead of the solid rods more commonly used.

Numerous modifications and variations of the present invention are possible in light of the above teachings. It is therefore to be understood that within the scope of the attendant claims appended thereto, this invention may be practiced otherwise than as specifically disclosed herein.

We claim:

1. An apparatus for examining and inspecting at least one sample, in order to determine the characteristics of the sample, the apparatus comprising:
   i) a support for receiving a compact disc, the compact disc having deposited on a surface thereof at least one sample;
   ii) an inspection means for effecting a physical change in at least one sample, the inspection means capable of moving translationally in at least one of an X direction and a Y direction and being positioned for registration with the surface of the compact disc bearing at least one sample;
   iii) a traversal mechanism adapted for reciprocating movement to move the sample in and out of the path of the inspection means; and
   iv) a scanning assembly that includes a plurality of ion guide rods fixed in a positioning guide, the ion guide rods defining an inlet at a first end proximate to the compact disc, an outlet at a second end proximate to an entrance to the apparatus, the positioning guide further having a lens situated within the positioning guide for allowing the passage of laser energy through the positioning guide.

2. The apparatus of claim 1 wherein the positioning guide is fixed in place.

3. The apparatus of claim 1 wherein the positioning guide is movable in at least one of an X direction and a Y direction.

4. The apparatus of claim 1 wherein the positioning guide is movable in the X direction and the Y direction.

5. The apparatus of claim 1 wherein the positioning guide, ion guide rods, and analytical device are movable in concert in at least one of an X direction and a Y direction.

6. The apparatus of claim 1 wherein the ion guide rods are constructed of a flexible material and the positioning guide and the first end of the ion guide rods are movable in at least one of an X direction and a Y direction.

7. The apparatus of claim 6 wherein the second end of the ion guide rods is fixed in place.

8. The apparatus of claim 1 wherein the ion guide rods are constructed of a flexible material and the positioning guide and the first end of the ion guide rods is movable in the X direction and the Y direction.

9. The apparatus of claim 6 wherein the second end of the ion guide rods is fixed in place.

10. The apparatus of claim 1 wherein the inspection means is capable of examining and inspecting information stored on the surface of the compact disk and wherein the apparatus is further comprised of a second inspection means for examining and inspecting information stored on a surface of the compact disc that is opposite the surface on which the sample is stored.

11. An analytical device for determining the properties of at least one sample of material, the analytical device comprising
   a base,
   a substrate adapted to be rotatably received by said base, said substrate having deposited thereon at least one sample of the material to be analyzed,
   an inspection means for effecting a physical change in at least one sample, the inspection means movably associated with said base,
   a translation system capable of movement in at least one of an X direction and a Y direction and adapted to effect a change in position between the inspection means and the substrate, causing the inspection means to register with the at least one sample on said substrate, at a predetermined location on said substrate, and
   a scanning assembly that includes a plurality of ion guide rods fixed in a positioning guide, the ion guide rods defining an inlet at a first end proximal to a compact disc, an outlet at a second end proximal to an entrance to the analytical device, the positioning guide further having a lens situated within the positioning guide for allowing the passage of laser energy through the positioning guide.

12. The analytical device of claim 11 wherein the positioning guide is fixed in place.

13. The analytical device of claim 11 wherein the positioning guide is movable in at least one of an X direction and a Y direction.

14. The analytical device of claim 11 wherein the positioning guide is movable in the X direction and the Y direction.

15. The analytical device of claim 11 wherein the positioning guide, ion guide rods, and analytical device are movable in concert in at least one of an X direction and a Y direction.

16. The apparatus of claim 11 wherein the ion guide rods are constructed of a flexible material and the positioning guide and the first end of the ion guide rods is movable in at least one of an X direction and a Y direction.

17. The apparatus of claim 16 wherein the second end of the ion guide rods is fixed in place.

18. The apparatus of claim 17 wherein the ion guide rods are constructed of a flexible material and the positioning guide and the first end of the ion guide rods are movable in the X direction and the Y direction.

19. The apparatus of claim 18 wherein the second end of the ion guide rods is fixed in place.

20. The analytical device of claim 11 further comprised of a second inspection means for examining and inspecting information stored on a surface of the compact disc that is opposite the surface on which the sample is stored.

* * * * *